(12) United States Patent
Schmidt

(10) Patent No.: US 6,467,485 B1
(45) Date of Patent: Oct. 22, 2002

(54) ANTI-SNORING DEVICE AND METHOD

(76) Inventor: Bruno Schmidt, 100 Cunningham Dr., New Smyrna Beach, FL (US) 32168

( * ) Notice: Subject to any disclaimer, the term of this patent is extended or adjusted under 35 U.S.C. 154(b) by 0 days.

(21) Appl. No.: 09/967,540

(22) Filed: Oct. 1, 2001

(51) Int. Cl.[7] .................................................. A61F 5/56
(52) U.S. Cl. ....................................... 128/848; 602/902
(58) Field of Search ................................ 128/846, 848, 128/859–862; 602/902

(56) References Cited

U.S. PATENT DOCUMENTS

| | | | | | |
|---|---|---|---|---|---|
| 5,649,549 A | * | 7/1997 | Saba | ........................... | 128/859 |
| 5,666,973 A | * | 9/1997 | Walter | ......................... | 128/860 |
| 5,915,385 A | * | 6/1999 | Hakimi | ........................ | 128/859 |
| 5,988,170 A | * | 11/1999 | Thomas | ....................... | 128/848 |

* cited by examiner

Primary Examiner—Michael A. Brown
(74) Attorney, Agent, or Firm—Stanley M. Miller

(57) ABSTRACT

An apparatus that inhibits snoring includes a handle and a distal free end that is disposed at an angle relative to the handle to facilitate placing the distal free end against the soft pallet at the back of a throat. A flexible material such as a sheet of paper is placed into overlying relation to the distal free end and a layer of adhesive is disposed in overlying relation to the paper. When the distal free end of the apparatus is pressed against the soft pallet, the adhesive quickly adheres to the soft pallet so that the paper adheres to the soft pallet when the apparatus is withdrawn. The paper provides rigidity that inhibits vibration of the soft pallet. Multiple layers of paper may be used. In an alternative embodiment, at least one layer of adhesive is applied to prevent vibration of the soft pallet and no paper is needed.

17 Claims, 2 Drawing Sheets

ANTI-SNORING DEVICE AND METHOD

BACKGROUND OF THE INVENTION

1. Field of the invention

This invention relates, generally, to devices and methods that help people stop snoring during sleep. More specifically, it relates to a device and method that applies a material to the soft pallet at the back of the mouth to inhibit vibration of the soft pallet as air flows past it.

2. Description of the prior art

It is known that certain surgical techniques can eliminate the cause of snoring in some people. However, surgery is a rather drastic, expensive remedy that is not without risk.

A well-known anti-snoring treatment available over-the-counter is an oil solution that is sprayed onto the back of the mouth. The oil mixture includes olive oil, sunflower oil, almond oil, peppermint oil, and the like. Oil soluble vitamins such as Vitamin E may also be provided in the solution. The oil apparently lubricates the soft pallet at the back of the mouth and perhaps the tongue as well and such lubrication solves the problem for some people. However, some people report unsatisfactory results with such oils.

Some people snore because they are overweight. In an effort to lose weight, they lower their intake of high fat foods. Accordingly, the addition of approximately one-teaspoon a day of high fat oil is undesirable.

Mechanical devices that suppress the tongue are also commercially available. These devices are about the size of a mouthpiece of the type worn by athletes engaged in contact sports. Many people find it difficult to sleep at night with such a device in their mouth. However, most of those who persist until they get used to the device are satisfied with the results.

What is needed, then, is a non-surgical alternative to oil-based and mouthpiece-reliant remedies. The alternative remedy that is needed should not require the user to ingest high fat oils or to get used to sleeping with a bulky mechanical structure in the mouth. Moreover, it should be effective, inexpensive and easy to use.

However, in view of the prior art taken as a whole at the time the present invention was made, it was not obvious to those of ordinary skill in this art how the needed device could be provided.

SUMMARY OF THE INVENTION

The long-standing but heretofore unfulfilled need for a non-surgical alternative to snoring that does not rely upon oils and mouthpieces is now met by a new, useful, and nonobvious applicator having an elongate handle and a distal free end. A flexible material having sufficient rigidity to inhibit vibration of a soft pallet when air flows past said soft pallet is disposed in overlying relation to the distal free end of the applicator and a thin layer of a non-toxic adhesive is disposed in overlying relation to the flexible material. The material is pressed against the soft pallet and the adhesive cures quickly so that the material is transferred from the distal free end of the applicator to the soft pallet when the applicator is withdrawn. The material adds sufficient rigidity to the soft pallet to inhibit vibration of the soft pallet when air flows past it during sleep.

An important object of this invention is to significantly advance the art of anti-snoring devices and methods by providing an applicator that adheres a snore-inhibiting appliance to the soft pallet at the back of a mouth.

A more specific object is to provide a method where snoring is inhibited by a piece of paper or similar flexible material that is adhered to the soft pallet.

Another important object is to provide a method that inhibits vibration of the soft pallet in the absence of paper or similar material.

The invention accordingly comprises the features of construction, combination of elements, and arrangement of parts that will be exemplified in the description set forth hereinafter, and the scope of the invention will be set forth in the claims.

BRIEF DESCRIPTION OF THE DRAWINGS

For a fuller understanding of the nature and objects of the invention, reference is made to the following detailed description, taken in connection with the accompanying drawings, in which.

DETAILED DESCRIPTION OF THE PREFERRED EMBODIMENT

Figure 1:
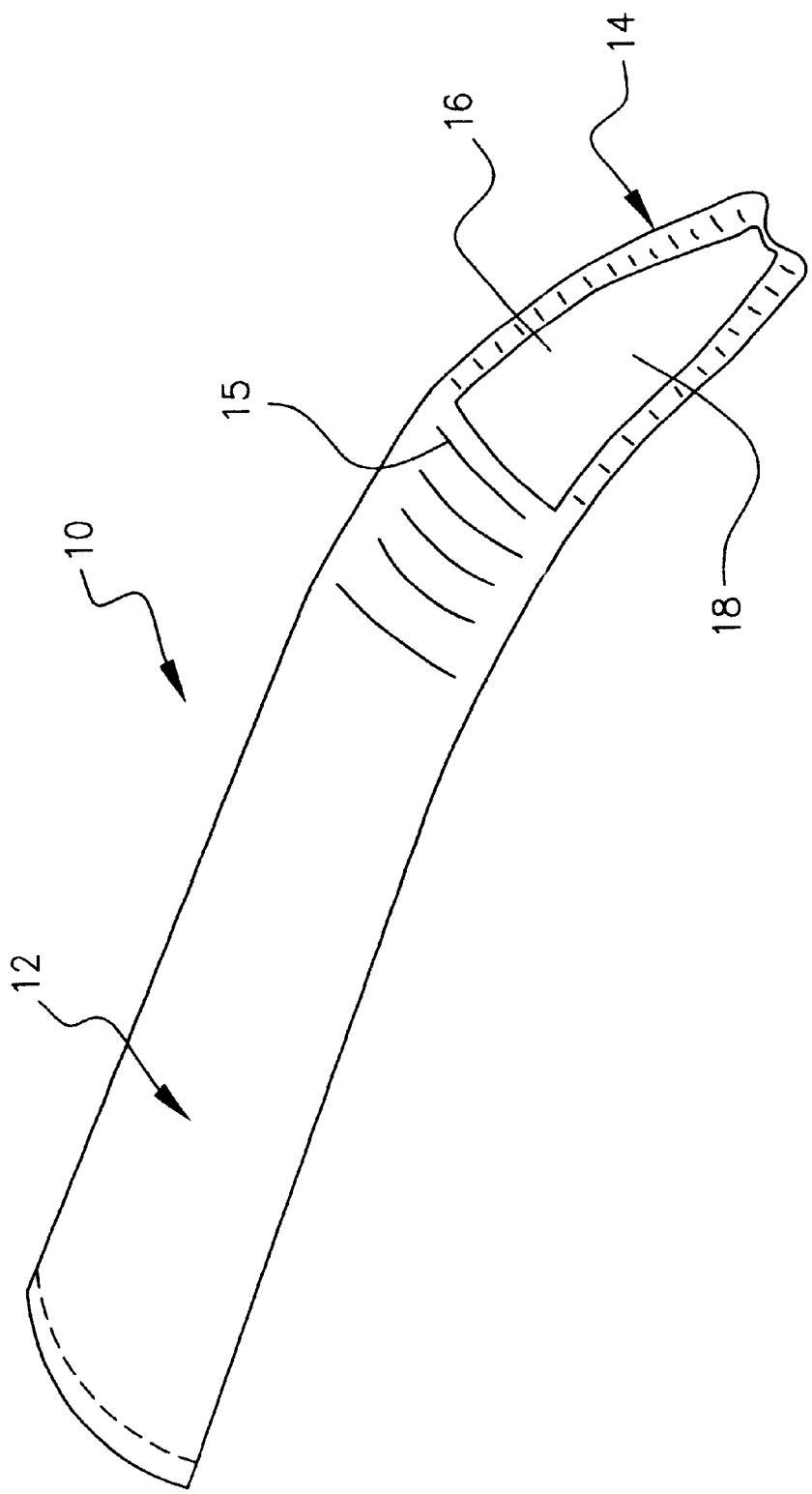
FIG. 1 is a perspective view of the novel device.

Referring now to FIG. 1, it will there be seen that an illustrative embodiment of the invention is denoted as a whole by the reference numeral 10.

Applicator 10 is of elongate construction and is approximately the size of a tongue depressor. Its handle is denoted 12 and its distal free end is denoted 14. Distal free end 14 is bent with respect to handle 12 as depicted to facilitate positioning said distal free end at the back of the mouth.

Both handle 12 and distal free end 14 have a convex curvature as depicted in FIG. 1 but this is not a critical feature of the invention. The convexity makes handle 12 comfortable to hold. The convexity of distal free end 14 is more important in that it enhances the function of the device as will become clear as this description proceeds.

In a first embodiment of the invention, a piece of paper 16 of predetermined configuration is positioned in overlying relation to distal free end 14. A thin layer of an adhesive, denoted 18, overlies paper 16. The adhesive is preferably bioabsorbable although the device will work with non-toxic, non-bioabsorbable adhesives. A cyanoacrylic adhesive is a suitable bioabsorbable adhesive. The adhesive is preferably of the very fast drying type.

A plurality of parallel, transversely disposed grooves, collectively denoted 15, may be formed in distal end 14 and the contiguous part of handle 12 to provide a non-slip support surface for paper 16.

In a commercial embodiment, thin layer of adhesive 18 is protected by a sheet of paper, not shown, that overlies the adhesive until such time as the device is ready to be used. The unillustrated sheet of paper is typically waxed or otherwise treated so that it is easily peeled from the adhesive. Such a structure is known in the adhesives industry as a "peel and seal" structure.

The overlying sheet of unillustrated waxed paper is discarded moments prior to application of paper 16 to the soft pallet at the back of the mouth. The mouth of the user is opened wide and distal free end 14 of appliance 10 is moved to the back of the mouth. Distal free end 14 is then displaced upwardly to cause adhesive 18 to contact the soft pallet. A little pressure may be applied to ensure that adhesive 18 takes hold, and appliance 10 is then removed from the mouth. The convexity of distal free end 14 helps it conform to the soft pallet and ensures that paper 16 and its overlying layer of adhesive 18 will come into firm contact with the soft pallet, unimpeded by distal free end 14.

Paper 16, or other suitable material, need not be strongly adhered to distal end 14. Paper 16 can simply be deposited atop distal free end 14 just prior to the application of said paper to the soft pallet. Alternatively, the bottom side of such paper 16 could be slightly moistened to prevent it from sliding off distal fee end 14 prior to installation of paper 16 to the soft pallet. A thin layer of adhesive could be used for the same purpose, but the holding power of such adhesive would have to be substantially less than the holding power of adhesive 18 so that paper 16 would release from distal free end 14 when adhesive 18 has cured.

In this first embodiment, the paper may be cellulose-based, rice-based, hemp-based, or the like. However, any flexible material, not limited to paper, that may be glued to the soft pallet may be used if the material has sufficient rigidity to prevent or inhibit vibration of the soft pallet as air flows over it during the deep breathing commonly associated with restorative, restful sleep. Merely changing the frequency of the soft pallet vibration may be sufficient to attenuate snoring sounds in some people.

Moreover, the material need not be perfectly flat like a sheet of paper, i.e., it may have strengthening ridges, corrugations, ripples, grooves, and the like, for example. However, the material is selected so that it is sufficiently thin to avoid interfering with breathing or swallowing.

In a second embodiment, the paper or other pliable material that supplies rigidity to the soft pallet is bioabsorbable. Ideally, the bioabsorbable material would degrade overnight so that the sleeper's mouth is empty when the sleeper awakens. The material could be impregnated with pleasant-tasting chemical or herbal compounds so that the sleeper awakens with a fresh and odor-free mouth. As suggested by the oil-based snoring remedies mentioned earlier, vitamins or other nutrients could also be delivered to the sleeper as the material dissolves overnight.

In both embodiments, the material used to provide rigidity to the soft pallet is preferably provided with a thin, flexible structure. In this way, a person with a soft pallet that needs very little rigidity to prevent vibration may use just one sheet of the material. A person having a soft pallet that requires more support could use two plies of the material, and so on. In this way, a commercially available product would supply a large number of sheets of material and those snorers who require less soft pallet support will not need to purchase new supplies of the material as frequently as those who must use multiple sheets of material each night.

The steps of the novel method of this invention include providing an applicator having a handle and a distal free end, positioning in overlying relation to said distal free end a flexible material having sufficient rigidity to inhibit vibration of a soft pallet when air flows past said soft pallet, applying a thin layer of a non-toxic adhesive in overlying relation to the flexible material, pressing the material against the soft pallet so that the material is transferred from the distal free end to the soft pallet when the adhesive cures and the applicator is withdrawn so that the material adds sufficient rigidity to the soft pallet to inhibit vibration of the soft pallet when air flows past it.

In a third embodiment, both the sheet of material 16 and applicator 10 are eliminated and a fast-drying, non-toxic adhesive is applied to the soft pallet by a suitable means such as an aerosol can, pump, or brush. The adhesive is preferably of the bioabsorbable type so that it is bioabsorbed within eight hours or so. As suggested by the first two embodiments, multiple layers of the adhesive may be built up in succession for those snorers requiring a higher degree of rigidity to prevent or attenuate vibration of their soft pallet.

In the embodiments where applicator 10 is used, a mild, spray-applied anesthetic such as Chloraseptic® throat spray may be applied to the back of the throat to inhibit or suppress a gag reflex that some people might experience when the soft pallet-reinforcing material is applied. No such gag reflex would be experienced when the third embodiment of this invention is employed.

Figure 2:
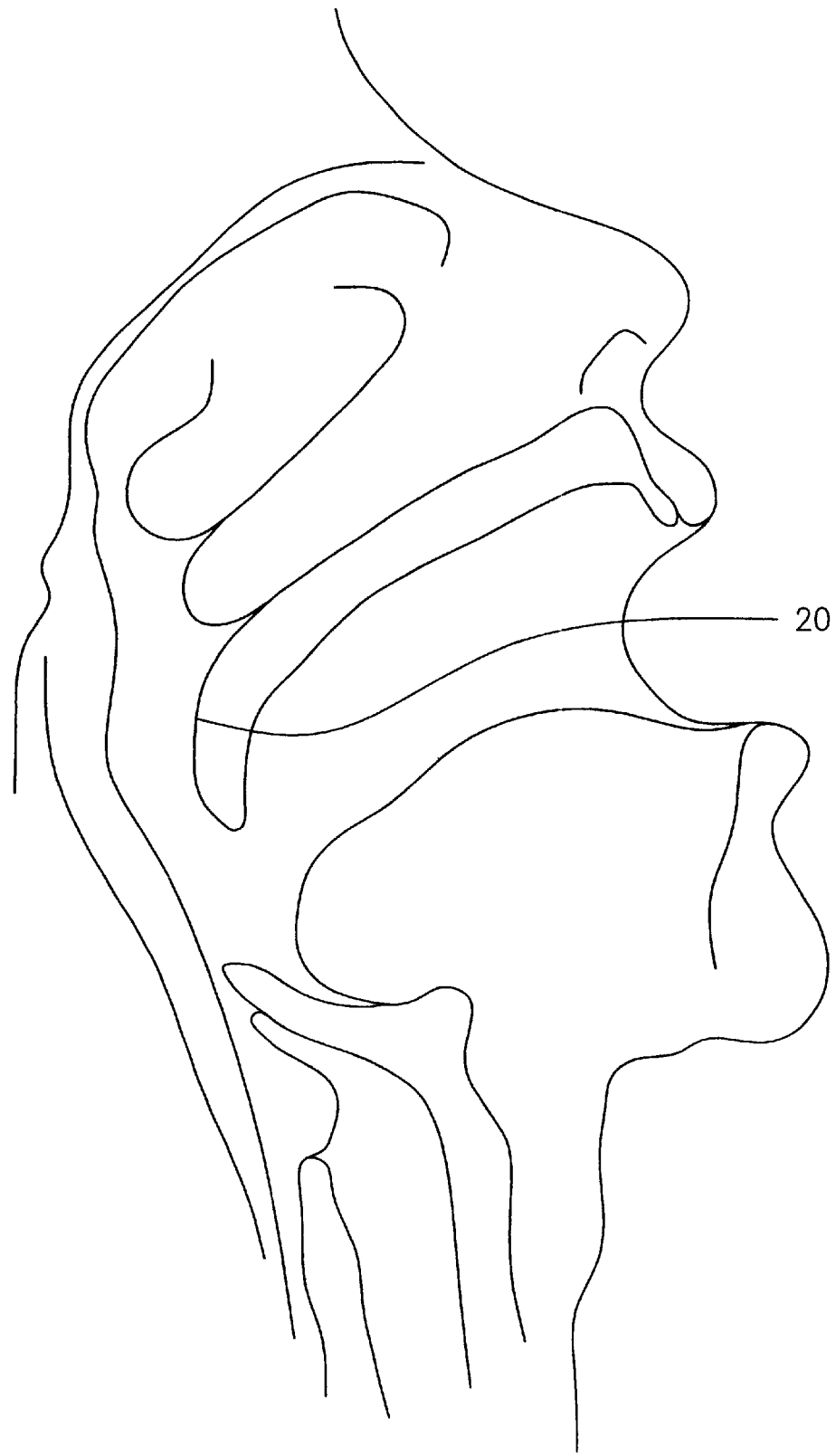
FIG. 2 is a side elevational view of a human head showing where the novel means for inhibiting vibration of the soft pallet is placed.

The placement of material 16 (first two embodiments) or the adhesive alone (third embodiment) is denoted in FIG. 2 by the reference numeral 20.

It will thus be seen that the objects set forth above, and those made apparent from the preceding description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A device that inhibits snoring, comprising:
an applicator having a handle and a distal free end;
a flexible material having sufficient rigidity to inhibit vibration of a soft pallet when air flows past said soft pallet;
said flexible material being disposed in overlying relation to said distal free end of said applicator;
a thin layer of a non-toxic adhesive disposed in overlying relation to said flexible material;
whereby said material is pressed against said soft pallet so that said material is transferred from said distal free end to said soft pallet when said adhesive adheres to said soft pallet;
whereby said material adds sufficient rigidity to said soft pallet to inhibit vibration of said soft pallet when air flows past said soft pallet.

2. The device of claim 1, wherein a bend is formed in said applicator so that said distal end is disposed in angular relation to said handle to facilitate placement of said material onto said soft pallet.

3. The device of claim 1, wherein said material is a cellulose-based paper.

4. The device of claim 1, wherein said material is a rice-based paper.

5. The device of claim 1, wherein said material is a hemp-based paper.

6. The device of claim 1, wherein said material is bioabsorbable.

7. The device of claim 1, wherein said adhesive is bioabsorbable.

8. The device of claim 1, wherein said material is impregnated with at least one preselected compound of the type that promotes a fresh and odor-free mouth at the end of a sleep period.

9. The device of claim 1, wherein said handle has a convex curvature.

10. The device of claim 1, wherein said distal free end has a convex curvature.

11. The device of claim 1, further comprising a plurality of parallel, transversely disposed grooves formed on said distal free end.

12. A method that inhibits snoring, comprising the steps of:
   providing an applicator having a handle and a distal free end;
   positioning in overlying relation to said distal free end a flexible material having sufficient rigidity to inhibit vibration of a soft pallet when air flows past said soft pallet;
   applying a thin layer of a non-toxic adhesive in overlying relation to said flexible material;
   pressing said material against said soft pallet so that said material is transferred from said distal free end to said soft pallet when said adhesive cures and said applicator is withdrawn so that said material adds sufficient rigidity to said soft pallet to inhibit vibration of said soft pallet when air flows past said soft pallet.

13. The method of claim 12, further comprising the step of forming a bend in said handle so that said distal free end is disposed in angular relation to said handle to facilitate placing said material in overlying relation to said soft pallet.

14. The method of claim 12, further comprising the step of repeating said positioning step at least once so that at least a second layer of said flexible material is disposed in overlying relation to said first-applied flexible material to increase the rigidity of said soft pallet.

15. A method that inhibits scoring, comprising the step of spraying a soft pallet with a non-toxic adhesive that increases the rigidity of said soft pallet when said adhesive cures.

16. The method of claim 15, further comprising the step of repeating said spraying step at least once after said first-sprayed adhesive has cured to further increase the rigidity of said soft pallet.

17. The method of claim 15, further comprising the step of spraying said soft pallet with a bioabsorbable adhesive.

* * * * *